(12) United States Patent
German et al.

(10) Patent No.: US 10,787,456 B2
(45) Date of Patent: Sep. 29, 2020

(54) OPIOID ANTAGONISTS AND METHODS RELATED THERETO

(71) Applicant: Texas Tech University System, Lubbock, TX (US)

(72) Inventors: Nadezhda German, Amarillo, TX (US); Mohammad Anwar Hossain, Amarillo, TX (US)

(73) Assignee: TEXAS TECH UNIVERSITY SYSTEM, Lubbock, TX (US)

( * ) Notice: Subject to any disclaimer, the term of this patent is extended or adjusted under 35 U.S.C. 154(b) by 0 days.

(21) Appl. No.: 16/175,540

(22) Filed: Oct. 30, 2018

(65) Prior Publication Data
US 2020/0131183 A1    Apr. 30, 2020

(51) Int. Cl.
| | |
|---|---|
| *A61K 31/407* | (2006.01) |
| *A61K 31/4985* | (2006.01) |
| *C07D 487/04* | (2006.01) |
| *A61P 25/32* | (2006.01) |
| *A61P 25/36* | (2006.01) |
| *A61P 25/02* | (2006.01) |

(52) U.S. Cl.
CPC ............ *C07D 487/04* (2013.01); *A61P 25/02* (2018.01); *A61P 25/32* (2018.01); *A61P 25/36* (2018.01)

(58) Field of Classification Search
CPC .............. A61K 31/407; A61K 31/4985; C07D 487/04; A61P 25/32; A61P 25/36; A61P 25/02
USPC .......... 514/250, 251; 548/428, 429; 544/344
See application file for complete search history.

(56) References Cited

PUBLICATIONS

Vigushin, D., G. Brooke, D. Willows, R. Coonnbes and C. Moody, "Pyrazino[1,2-a]indole-1,4-diones, Simple Analogues of Gliotoxin, as Selective Inhibitors of Geranylgeranyltransferase I" Bioorg. Med. Chem. Lett. (2003), 13(21), pp. 3661-3663. (Year: 2003).*
[NPL1] Alan D. Borthwick. 2,5-Diketopiperazines: Synthesis, Reactions, Medicinal Chemistry, and Bioactive Natural Products. Chemical Reviews 2012, 112(7), 3641-3716.
[NPL2] T.R. Welch, R.M. Williams. Epidithiodioxopiperazines. occurrence, sysnthesis and biogenesis. Nat. Prod. Rep., 2014, 31(10), 1376-1404.
[NPL3] Scharf, D. H.; Remme, N.; Heinekamp, T.; Hortschansky, P.; Brakhage, A. A.; Hertweck, C. Transannular Disulfide Formation in Gliotoxin Biosynthesis and Its Role in Self-Rresistance of the Human Pathogen Aspergillus fumigatus. J. Am. Chem. Soc. 2010, 132, 10136-10141.
[NPL4] Cornacchia C, Cacciatore I, Baldassarre L, Mollica A, Feliciani F, Pinnen F. 2,5-diketopiperazines as neuroprotective agents. Mini-Rev Med Chem. 2012;12:2-12.
[NPL5] Faden Al, Holaday JW. Opiate antagonists: A role in the treatment of hypovolemic shock. Science. 1979, 205:317-318.

* cited by examiner

*Primary Examiner* — Matthew P Coughlin
*Assistant Examiner* — Sagar Patel
(74) *Attorney, Agent, or Firm* — Dickinson Wright PLLC; Krisopher Lance Anderson

(57) ABSTRACT

Disclosed is a composition and method for a therapeutic treatment that is able to combat certain conditions such as alcohol dependence, opioid abuse treatment, neurological disorders, neuropathic pain, and fibromyalgia. The novel gliotoxin analog compound acts by acting as an antagonist to one or more opioid receptors, which, when present leads to the inhibition of conditions, providing increased performance over known treatments. The disclosed compounds also shows the ability to cross the blood-brain-barrier in a highly efficient manner.

22 Claims, 8 Drawing Sheets

OPIOID ANTAGONISTS AND METHODS RELATED THERETO

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

CROSS-REFERENCE TO RELATED APPLICATIONS

None.

TECHNICAL FIELD

The present invention relates in general to the field of therapeutic treatment. In particular, the present invention provides for a novel class of chemical compounds with non-selective opioid antagonist properties. The disclosed compounds have potential to be used in patients with certain opioid and substance abuse as well as chronic pain.

STATEMENT OF FEDERALLY FUNDED RESEARCH

None.

BACKGROUND OF THE DISCLOSURE

Opioid receptors are inhibitory receptors with opioids as ligands. Opioid receptors are widely distributed in the brain and are also found throughout the spinal cord. There are 3 major subtypes of opioid receptors know as delta, kappa, and mu opioid receptors. These receptors are the targets of opium derived drugs known as opioids. Opioids are used for pain relief and anesthesia. Since opioids can produce strong feelings of euphoria, they are commonly used in a recreational setting, and are subject to abuse and addiction. In 2014 almost 2 million Americans abused and were dependent on prescription opioids, and in 2016 64,000 people died of an overdose of opioids. There is a major need for solutions to the increase in opioid usage.

Opioid receptor antagonists are a class of drugs that work by antagonizing or inhibiting the function of opioid receptors. These drugs work by competitively binding to the ligand receptor site of opioid receptors. This competitive inhibition does not allow opioid drugs to bind and thus, they have no effect. Certain opioid antagonists have such a high affinity for opioid receptors that they will displace the opioid drug from the receptor reversing its effect. There are several opioid antagonists currently used in the clinical setting. Naloxone and naltrexone are among the most common and are effective at treating opioid overdose and mitigating the effects of opioids and may be used to treat opioid dependency. However, there remains a need in the art to develop superior alternatives to current drugs on the market.

SUMMARY OF THE DISCLOSURE

The present invention addresses failings in the art by providing compositions of gliotoxin (see FIG. 1) derivatives capable of serving as a non-selective opioid receptor antagonist, as well as methods for a therapeutic treatment that utilizes such compounds as opioid receptor antagonists. Gliotoxin was first discovered in 1936 as the secondary metabolite from the opportunistic fungi, *Gliocladium fimbriatum*, as well as from several other fungal species. Gliotoxin has been reported as an antifungal agent, antimicrobial agent, anticancer agent, antiviral agent and immunomodulatory agent. However, it has equivocal toxicity and therapeutic effects in humans and animals.

The novel compounds of the present invention are derivatives of gliotoxin which address the known toxicity effects of gliotoxin, primarily due to the presence of a disulfide bridge and function via generation of reactive oxygen species (ROS) and mixed disulfide formation. The novel compounds of the present invention also show the ability to cross the blood-brain-barrier (BBB) where many opioid receptors are present. This novel class of compounds has the potential to be a powerful new treatment to combat conditions such as general opioid abuse, alcohol dependence, neuropathic pain, fibromyalgia, and other chronic pain conditions.

It is therefore and object of the present invention to provide gliotoxin derivative compounds which do not have a disulfide bridge present. In one aspect of the present invention, a molecule is derived from gliotoxin that has immunosuppressive capabilities. The opioid antagonist compounds of the present invention offer a new class of antagonists that are structurally different from known compounds. In addition, it may offer an increase in the duration of action of the drug since it exhibits a longer half-life.

In one aspect, the present invention provides a compound of substituted gliotoxin derivatives, or a pharmaceutically acceptable salt thereof. In another aspect, the present invention provides a compound comprising (4-ethyl-8-methyl-7,8,9a,10-tetrahydropyrido[1,2-α]indole-6,9-dione) (see FIG. 3), or a pharmaceutically acceptable salt thereof or isotopic variants thereof, stereoisomers or tautomers thereof.

In another aspect, the present invention provides a pharmaceutical formulation comprising an effective amount of a compound (4-ethyl-8-methyl-7,8,9a,10-tetrahydropyrido[1,2-α]indole-6,9-dione) (see FIG. 3) sufficient as a non-selective antagonist of opioid receptors. In another aspect, said compound is capable of having at least 50% of the administered amount cross the blood-brain barrier (BBB) of a patient. In yet another aspect, said compound is capable of having at least 80% of the administered amount cross the BBB of a patient. The compound of the present invention is effective to treat alcohol dependence, opioid abuse treatment, neurological disorders, neuropathic pain, and fibromyalgia, and is capable of inhibition of CNS receptors including the mu (μ) opioid receptor, delta (δ) opioid receptor, or the kappa (κ) opioid receptor, or combinations therein. The compound of the present invention is further effective to block or reduce the tolerance of said mammal to an opioid receptor agonist, such as morphine, methadone, codeine, diacetyl morphine, morphine-N-oxide, oxymorphone, oxycodone, hydromorphone, hydrocodone, meperidine, heterocodeine, fentanyl, sufentanil, levo-acetylmethadol, alfentanil, levorphanol, tilidine, diphenoxylate, hydroxymorphone, noroxymorphone, metopon, propoxyphene, and the pharmaceutically acceptable salts thereof.

In another aspect of the present invention, a method is provided for treating a disorder selected from the group consisting of alcohol dependence, opioid abuse treatment, neurological disorders, neuropathic pain, and fibromyalgia, comprising administering to a patient a therapeutically effective amount of a compound (4-ethyl-8-methyl-7,8,9a,10-tetrahydropyrido[1,2-α]indole-6,9-dione) (see FIG. 3) or a pharmaceutically acceptable salt thereof or isotopic variants thereof, stereoisomers or tautomers thereof. In another aspect a method for of treating a mammal is provided comprising the step of: administering to a patient a pharmaceutical acceptable amount of a compound (4-ethyl-8-methyl-7,8,9a,10-tetrahydropyrido[1,2-α]indole-6,9-dione) (see FIG. 3) or a pharmaceutically acceptable salt thereof or isotopic variants thereof, stereoisomers or tautomers thereof, wherein said pharmaceutically acceptable amount is effective as an antagonist to one or more opioid receptors.

In another aspect the compound comprises an aqueous solution and one or more pharmaceutically acceptable excipients, additives, carriers or adjuvants. In another aspect the compound further comprises one or more excipients, carriers, additives, adjuvants, or binders in a tablet or capsule.

In another aspect the compound is administered via an oral, intraperitoneal, intravascular, peripheral circulation, subcutaneous, intraorbital, ophthalmic, intraspinal, intracisternal, topical, infusion, implant, aerosol, inhalation, scarification, intracapsular, intramuscular, intranasal, buccal, transdermal, pulmonary, rectal, or vaginal route.

BRIEF DESCRIPTION OF THE DRAWINGS

The foregoing and other objects, features, and advantages of the disclosure will be apparent from the following description of embodiments as illustrated in the accompanying drawings, in which reference characters refer to the same parts throughout the various views. The drawings are not necessarily to scale, emphasis instead being placed upon illustrating principles of the disclosure:

FIGS. 8A-8C depict charts showing CNS activity of the gliotoxin analog of the present invention, wherein FIG. 8A shows inhibition of the Mu Opiod receptor (MOR), FIG. 8B shows inhibition of the Delta Opioid receptor (DOR), and FIG. 8C shows inhibition of the Kappa Opioid receptor (KOR).

DETAILED DESCRIPTION OF THE DISCLOSURE

Figure 1:
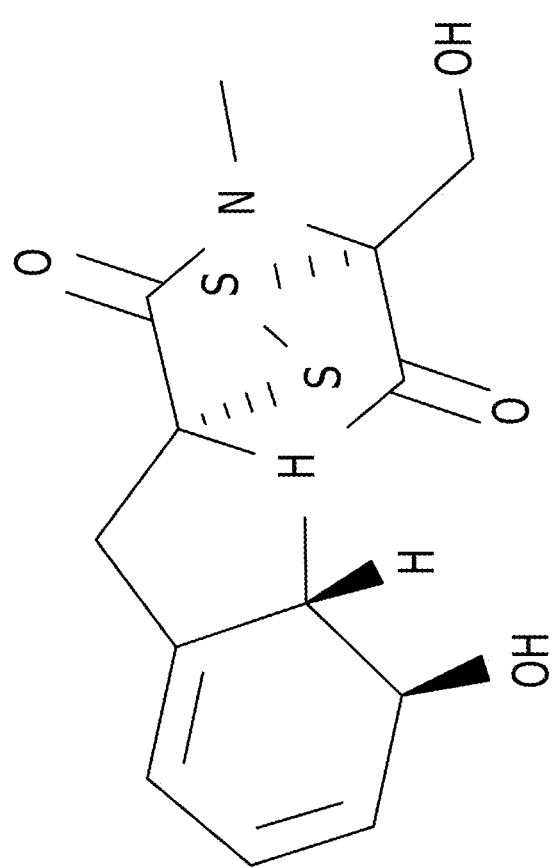
FIG. 1 depicts the chemical structure for gliotoxin.

While the making and using of various embodiments of the present invention are discussed in detail below, it should be appreciated that the present invention provides many applicable inventive concepts that can be embodied in a wide variety of specific contexts, goods, or services. The specific embodiments discussed herein are merely illustrative of specific ways to make and use the disclosure and do not delimit the scope of the disclosure.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The present invention will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, compositions, or systems. Accordingly, embodiments may, for example, take the form of methods, compositions, compounds, materials, or any combination thereof. The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The term "treating" refers to reversing, alleviating, or inhibiting the progress of a disease, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a compound or composition of the present invention to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

The terms "subject", "individual", or "patient" are used interchangeably herein and refer to an animal preferably a warm-blooded animal such as a mammal. Mammal includes without limitation any members of the Mammalia. In general, the terms refer to a human. The terms also include domestic animals bred for food or as pets, including equines, bovines, sheep, poultry, fish, porcines, canines, felines, and zoo animals, goats, apes (e.g. gorilla or chimpanzee), and rodents such as rats and mice.

Figure 3:
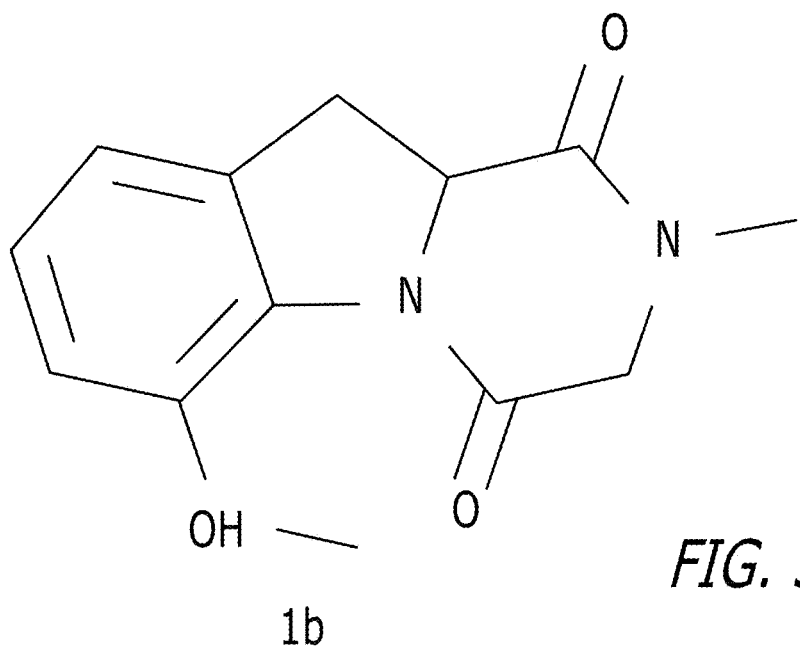
FIG. 3 depicts the chemical structure for the gliotoxin analog of the present invention.

Compound (4-ethyl-8-methyl-7,8,9a,10-tetrahydropyrido[1,2-α]indole-6,9-dione) (see FIG. 3), can exist in unsolvated as well as solvated forms with pharmaceutically acceptable solvents such as water, ethanol, and the like. The solvated forms may be considered equivalent to the unsolvated forms for the purposes of the present invention.

"Therapeutically effective amount" relates to the amount or dose of an active compound of (4-ethyl-8-methyl-7,8,9a,10-tetrahydropyrido[1,2-α]indole-6,9-dione) (see FIG. 3), or a composition comprising the same, that will lead to one or more desired effects, in particular, one or more therapeutic effects, more particularly beneficial effects. A therapeutically effective amount of a substance can vary according to factors such as the disease state, age, sex, and weight of the subject, and the ability of the substance to elicit a desired response in the subject. A dosage regimen may be adjusted to provide the optimum therapeutic response (e.g. sustained beneficial effects). For example, several divided doses may be administered daily or the dose may be proportionally reduced as indicated by the exigencies of the therapeutic situation.

The term "pharmaceutically acceptable carrier, excipient, or vehicle" refers to a medium which does not interfere with the effectiveness or activity of an active ingredient and which is not toxic to the hosts to which it is administered. A carrier, excipient, or vehicle includes diluents, binders, adhesives, lubricants, disintegrates, bulking agents, wetting or emulsifying agents, pH buffering agents, and miscellaneous materials such as absorbents that may be needed in order to prepare a particular composition. Examples of carriers etc. include but are not limited to saline, buffered saline, dextrose, water, glycerol, ethanol, and combinations thereof. The use of such media and agents for an active substance is well known in the art.

Gliotoxin (see FIG. 1) is a well-known and well-studied metabolite identified is a member of the epipolythiodioxopiperazine class of toxins and is both the major and the most potent toxin produced by multiple opportunistic fungi, such as *Gliocladium fimbriatum* and *Aspergillus fumigatus*. Gliotoxin has chemical features: (1) epidithiopiperazine ring; (2) a disulfide bridge; (3) a dehydrobenzene ring; (4) stereo structure; and (5) a bicyclic ring.

The core structure of gliotoxin contains a diketopiperazine (DKP) moiety, a naturally privileged structure. DKP has been reported as GPCR modulator, neuroprotective agent after traumatic brain or spinal cord injury. However, due to the presence of a disulfide bridge, certain toxicity effects are observed. It has been determined with the present invention that removal of the disulfide bridge yields analogs of gliotoxin with potential neuroprotective activity.

Figure 2:
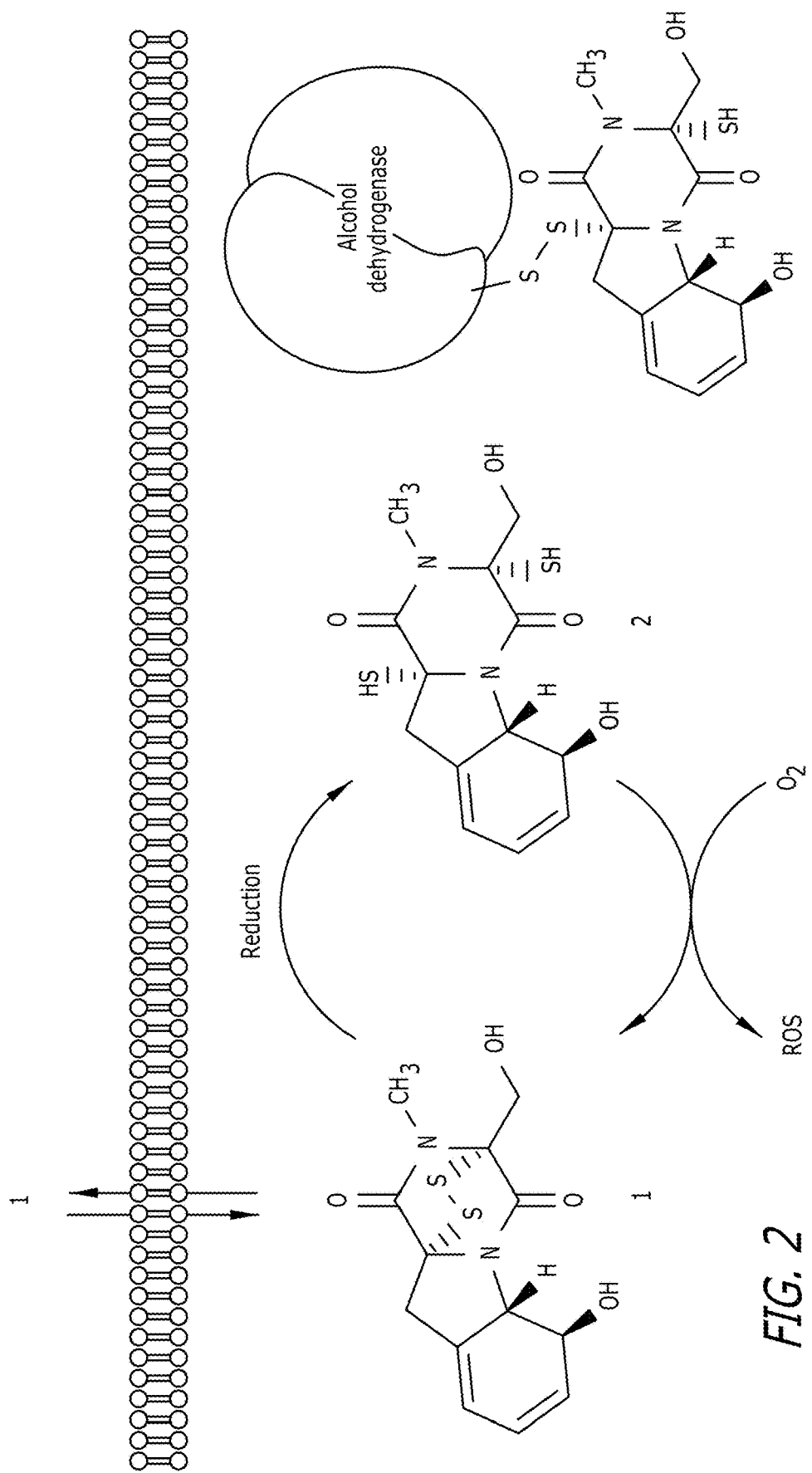
FIG. 2 depicts gliotoxin action inside the host cell: redox cycling resulting in formation of reactive oxygen species (ROS), and protein conjugation.

Turning to FIG. 2, exemplary action of gliotoxin inside a host cell indicates the redox cycling resulting in the formation of reactive oxygen species (ROS) and protein conjugation. Toxicity of the has been attributed to the presence of the disulfide bridge and function via generation of reactive oxygen species and mixed disulfide formation.

It is therefore an embodiment of the present invention to provide novel derivative compounds of gliotoxin, or pharmaceutically acceptable salts thereof, are presented for treating certain disorders in a patient, such as alcohol dependence, opioid abuse treatment, neurological disorders, neuropathic pain, and fibromyalgia. It is one embodiment of the present invention to provide a compound (4-ethyl-8-methyl-7,8,9a,10-tetrahydropyrido[1,2-α]indole-6,9-dione) (see FIG. 3), referred to herein as Formula 1b. It is another embodiment of the present invention to provide pharmaceutically acceptable compositions comprising compounds of Formula 1b, and a pharmaceutically acceptable carrier.

Another embodiment of the present invention relates to a method for providing neuroprotection in a mammal in need of such treatment. The method comprises administering to the mammal a therapeutically effective amount of a compound of Formula 1b or a pharmaceutically acceptable salt thereof. In another embodiment, the present invention provides a pharmaceutical composition comprising a therapeutically effective amount of a compound of the invention or a pharmaceutically acceptable salt thereof in combination with one or more pharmaceutically acceptable carriers. The composition is preferably useful for the treatment of the disease conditions described above.

Further, the present invention provides the use of a compound of Formula 1b or a pharmaceutically acceptable salt thereof, in the manufacture of a medicament for the treatment of the disease conditions described above.

In another embodiment, the compounds, compositions, and methods disclosed herein therefore may be utilized to prevent and/or treat a disease such as alcohol dependence, opioid abuse treatment, neurological disorders, neuropathic pain, and fibromyalgia, among other conditions mediated by one or more opioid receptors.

In an illustrative embodiment of the present invention, gliotoxin and Formula 1b, were evaluated for activity of various receptors. Turning to Table 1, inhibitory data is provided for various receptors found in the CNS, including H1 and opioid receptors μ (MOR), σ (DOR), and κ (KOR). Inhibition data is provided as inhibitor constant, Ki, is the concentration required to produce half-maximum inhibition. This quantitative measure indicates how much of a particular drug or other substance (inhibitor) is needed to inhibit a given biological process (or component of a process, i.e. an enzyme, cell, cell receptor or microorganism) by half. The values are typically expressed as molar (micro- and nano-) concentrations.

TABLE 1

Inhibitory data relating to MOR, DOR, and KOR inhibition of gliotoxin and the gliotoxin analog - Formula 1b of the present invention.

| GPCRs | Gliotoxin | | 1b | | | |
| --- | --- | --- | --- | --- | --- | --- |
| | H1 | Opioid | H1 | μ (MOR) | σ (DOR) | κ (KOR) |
| Ki | 423 | NA | NA | 262 | 148 | 197 |
| Inhibition (%) | 61% | NA | NA | 97.8 | 97.4 | 99.3 |

In one embodiment, compound of the present invention Formula 1b, along with gliotoxin, are shown Table 1 to show inhibition with regard to various receptors, including H1 and opioid receptors μ (MOR), σ (DOR), and κ (KOR).

Further cytotoxicity studies show potential for efficacy as an opioid receptor antagonist. Table 2, below, provides $IC_{50}$ data relating to both a cancer cell line and *E. coli* minimum inhibitory concentration (MIC).

TABLE 2

Inhibitory data relating to cancer cell line MDA-MB-231 and *E. Coli* inhibition of gliotoxin and the gliotoxin analog - Formula 1b of the present invention.

|  | Gliotoxin | Formula 1b |
|---|---|---|
| MDA-MB-231 IC$_{50}$ | 1.4 µM | >100 µM (not active) |
| *E. Coli* MIC | 32 µg/ml | Not Active |
| CNS Receptor binding | H1 Receptor Antagonist | Opioid Antagonist |

Figure 4:
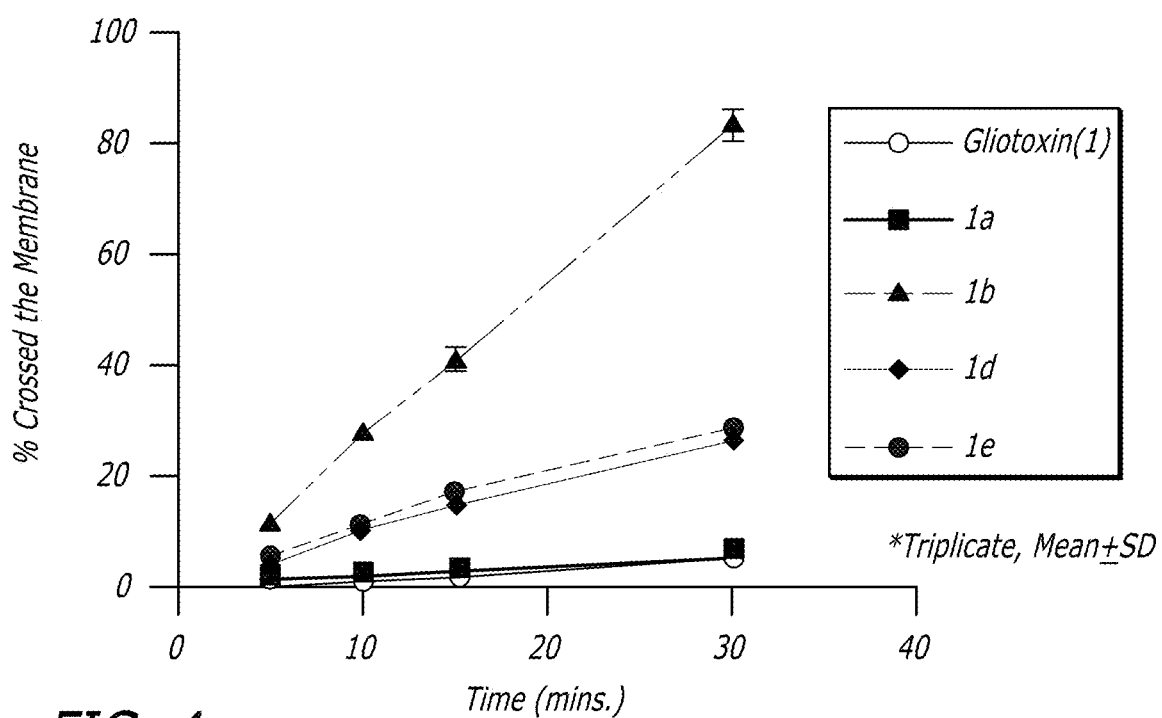
FIG. 4 depicts a chart showing membrane permeability as a function of time, wherein 1b is the gliotoxin analog of the present invention.

FIG. 4 provides permeability data for the blood-brain barrier (BBB) of various compounds, including gliotoxin and Formula 1b. Membrane permeability increases linearly as a function of time. Gliotoxin derivatives lacking disulfide bridges showed 15-20 times increased permeability in in-vitro monolayer of bEnd.3 cells mimicking the blood brain barrier. This suggests very high ability of Formula 1b to cross the BBB (80% in 30 minutes).

Figure 5:
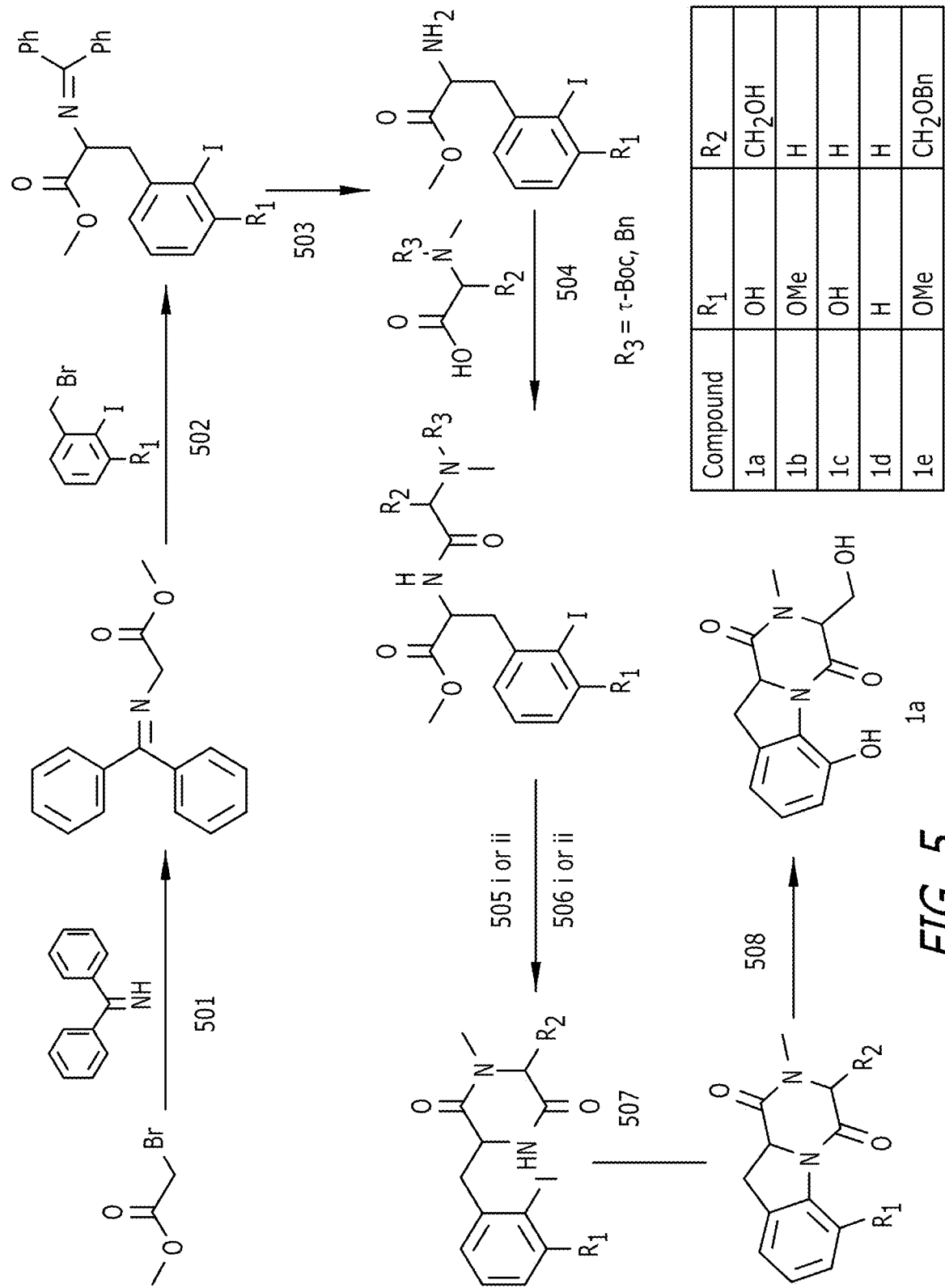
FIG. 5 depicts the general method for gliotoxin analog manufacture.

FIG. 5 shows an example of a process for synthesizing 1(4-ethyl-8-methyl-7,8,9a,10-tetrahydropyrido[1,2-α]indole-6,9-dione). Step 501. A solution of methyl bromoacetate (5.5 g, 35.9 mmol) in acetonitrile (40 mL) was treated with benzophenonimine (6.5 g, 35.8 mmol) and diisopropylethylamine (6.2 mL, 4.6 g, 35.6 mmol). The resulted mixture was heated at reflux (90° C.) for 12 hours. After reaction completion, the mixture was cooled to room temperature and concentrated in vacuo. The formed residue was partitioned between water (40 mL) and diethyl ether (60 mL), and the organic portion was separated, dried over MgSO4, filtered, and concentrated in vacuo. The product was purified by flash column chromatography and eluted with ethyl acetate/hexane to obtain white crystals (70%).

Step 502. KOtBu (0.484 g, 4.3 mmol) was suspended in THF (18 mL) and the mixture was cooled to −78° C. A solution of imine (0.916 g, 3.6 mmol) in THF (18 mL) was added via cannula to the suspension and allowed to stir for 30 min, followed by addition of a solution of benzyl bromide (1.3 g, 3.97 mmol) in THF (18 mL) via cannula. After 5 h the reaction mixture was warmed to room temperature, water (40 mL) was added, and THF portion was removed in vacuo. The aqueous solution was extracted with CH2Cl2 (3×20 mL), and the combined organics were washed with brine (40 mL), dried with Na2SO4, filtered and concentrated in vacuo. The crude material was purified by flash chromatography (5% Et2O/benzene) to provide the title compound as a light-yellow solid (47%).

Step 503. 10% aq. solution of citric acid (32 mL) was added to a solution of imine (step B, 4.82 g, 9.65 mmol) in THF (97 mL), and reaction mixture was allowed to stir for 16 h. then the reaction was diluted with Et2O (40 mL) and extracted with 1 N HCl (2×30 mL). The acidic solution was washed with Et2O (2×30 mL) and basified with solid K2CO3. The basic aqueous solution was extracted with EtOAc (3×30 mL), washed with brine (50 mL), dried with MgSO4, filtered and concentrated in vacuo to yield crude (90% yield), which was used in the next step as is.

Step 504. Et3N (1.25 mL, 8.95 mmol) was added to a solution of amine (step C, 3.00 g, 8.95 mmol), respective N-substituted amino acid (10.7 mmol), and EDCI (1.72 g, 8.95 mmol) in CH2Cl2 (18 mL), and the reaction mixture was allowed to stir for 20 h. After completion of the reaction, mixture was diluted with CH2Cl2 (20 mL) and washed with 10% aq. HCl (20 mL), followed by a wash with sat. aq. NaHCO3 (2×20 mL). The combined aqueous portions were extracted with CH2Cl2 (2×20 mL), and organic extracts were combined, washed with brine (50 mL), dried over Na2SO4, filtered and concentrated in vacuo. The crude material was purified by flash chromatography (15:1 CH2Cl2:MeOH) to give desired dipeptide (30-90%).

Step 505(*i*). Dipeptide (from step d) was dissolved in CH2Cl2 (90 mL), and TFA (4.1 mL, 53.7 mmol) was added. The reaction mixture was stirred overnight. After no starting material was detected, the reaction solvent was removed in vacuo. The crude residue was purified by flash chromatography (12:1 CH2Cl2:MeOH) yielding 86% product.

Step 505(*ii*). CAN was added portion wise to a stirred solution of the corresponding dipeptide (step d) (1.0 equiv.) in a solution of MeCN—H2O (5:1) and stirring continued for 16 hours at room temperature. After completion, the reaction was quenched by the addition of saturated aqueous sodium bicarbonate solution and stirred vigorously for 10 minutes, followed by extraction first with DCM. The combined organic portions were dried over MgSO4, filtered and concentrated in vacuo before purification by column chromatography (30%).

Step 506(*i*). The deprotected dipeptide [step E (i)] (2.11 g, 5.2 mmol) was dissolved in MeOH (54 mL), and NH4OH (28% in water, 5.36 mL) was added to the reaction mixture. The reaction mixture was stirred for 1 h, and the solvent was removed in vacuo. The crude material was purified by flash chromatography (12:1 CH2Cl2:MeOH) to provide diketopiperazine (75%).

Step 506(*ii*). The deprotected dipeptide [step E (ii)] in toluene was stirred for 5 days at 130° C. in a pressure vessel. The reaction solvent was removed in vacuo and formed residue was purified by flash chromatography using ethyl acetate/hexane eluent system (70%).

Step 507. DMEDA (87.2 µL, 0.82 mmol) was added to the solution containing aryl iodide [step F (i) or (ii)] (4.1 mmol), CuI (0.078 g, 0.41 mmol), and K3PO4 (1.741 g, 8.2 mmol) in toluene (41 mL). The reaction mixture was heated at 110° C. for 12 h then cooled to room temperature, filtered, and reaction solvent was removed in vacuo. The crude material was purified using filtration via a plug of silica gel (15:1 CH2Cl2:MeOH) to yield desired tricyclic diketopiperazine (40-80% yield).

Step 508. Boron trichloride (0.13 mL) was added to a solution of O-benzyl protected diketopiperazine (step g) (0.0730 mM) in CH2Cl2 (8 mL) at room temperature. The reaction solution was continued to stir at room temperature for 20 mins and then poured into ice water. The aqueous layer was thoroughly extracted with CH2Cl2. The combined organic portions were dried over anhydrous sodium sulfate, filtered and evaporated to give the final product in the form of crystals (90%).

Figures 6A, 6B, 6C:
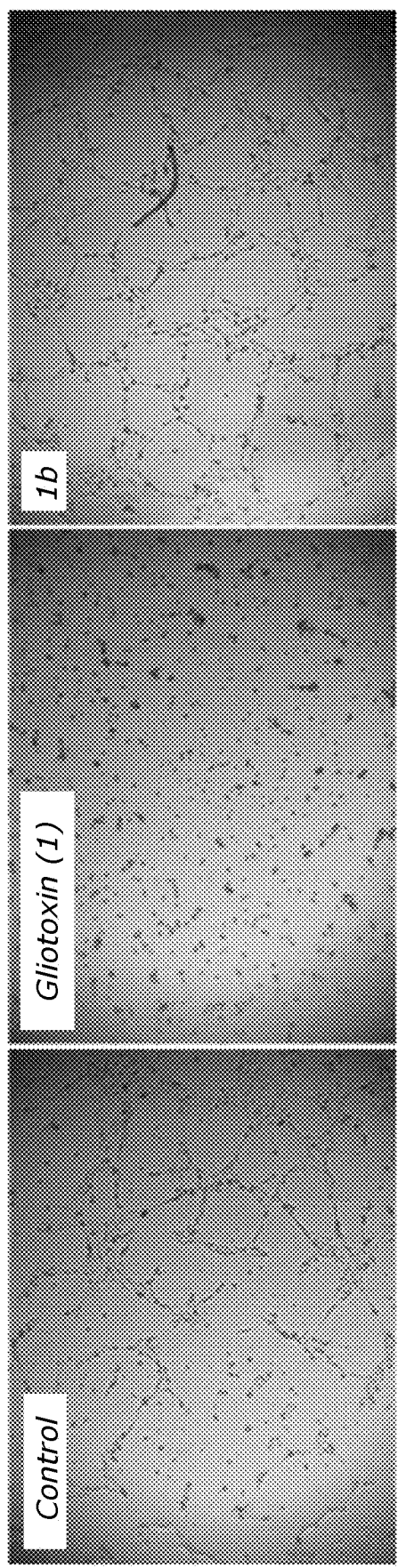
FIGS. 6A-6C depict tube formation in HUVEC in presence of 100 nM of drug treatment for control (FIG. 6A), gliotoxin (FIG. 6B), and the gliotoxin analog of the present invention (FIG. 6C).

Angiogenesis studies were performed using HUVEC cells (see FIGS. 6A-6C). Tube formation in HUVEC in presence of 100 nM of drug treatment. Inhibition of tube formation was observed in gliotoxin treatment but no inhibition was observed in the control or with Formula 1b treatment.

Figure 7:
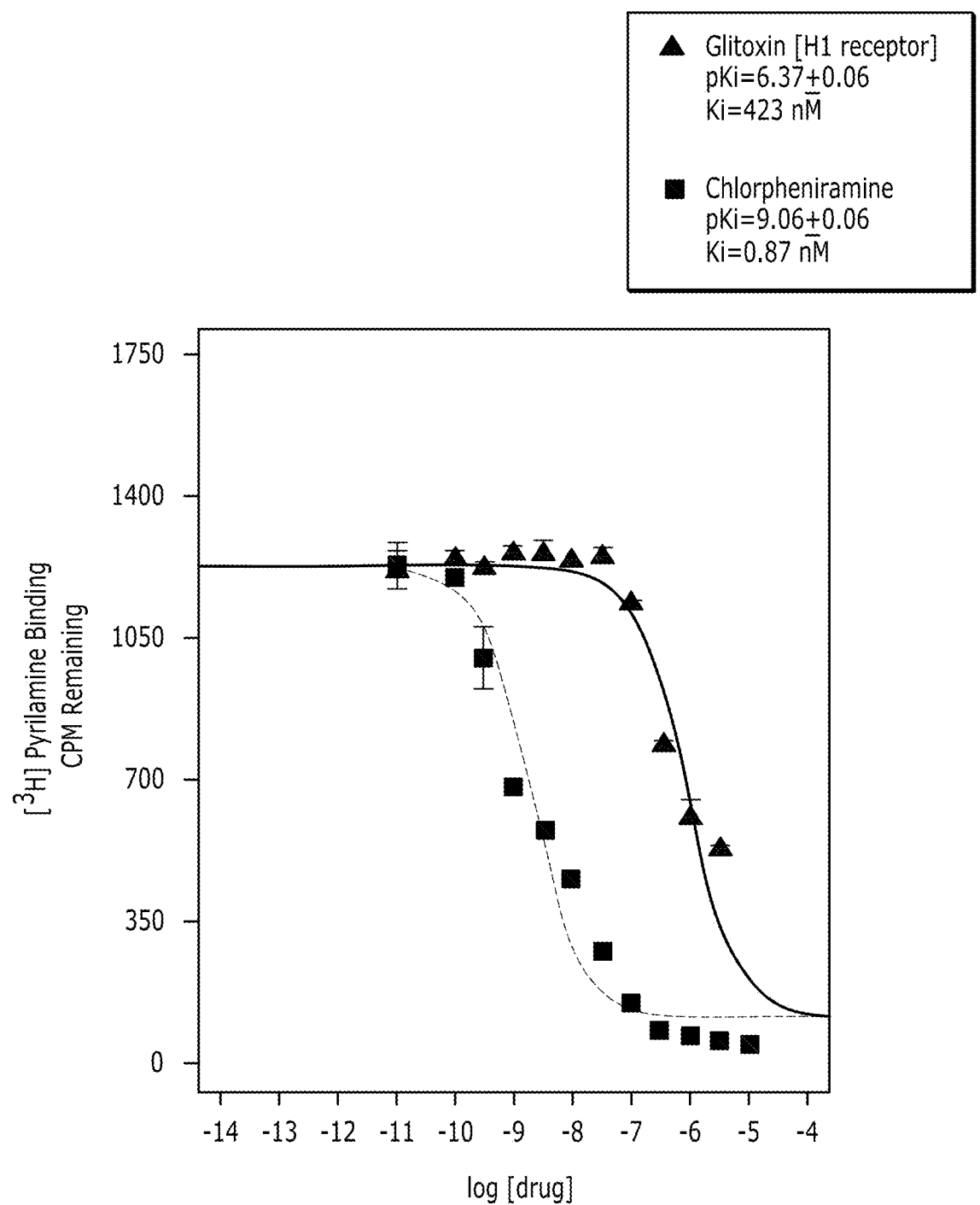
FIG. 7 depicts a chart showing CNS activity of gliotoxin—partial inhibition of the H1 receptor.
Figures 8A, 8B, 8C:
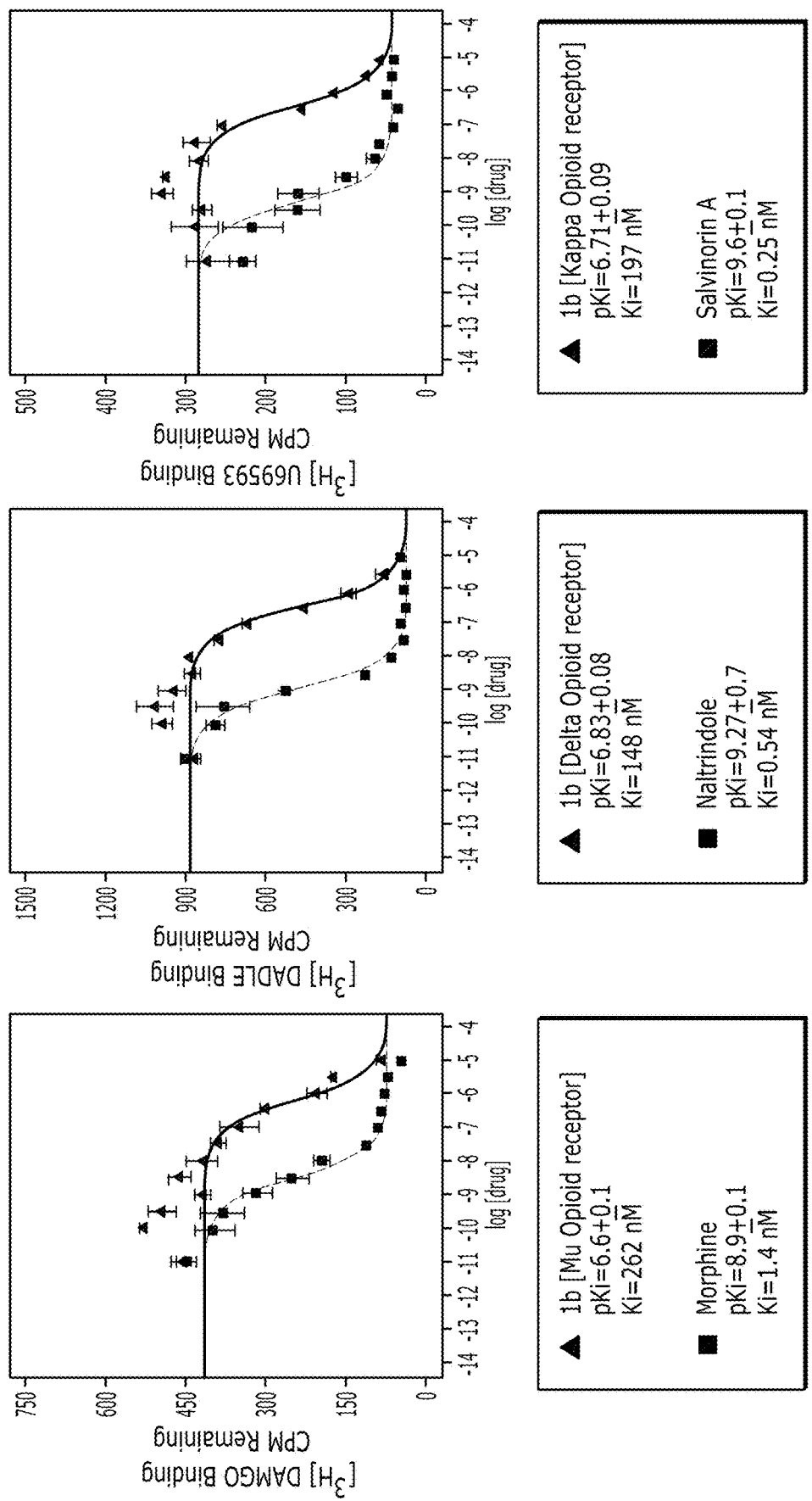

Additional studies were performed for CNS receptor inhibition. FIG. 7 shows inhibition of the H1 receptor by gliotoxin. FIG. 8A shows inhibition of the Mu Opioid Receptor compared to activity of morphine. FIG. 8B shows inhibition of the Delta opioid receptor compared to naltrindole. FIG. 8C shows inhibition of the Kappa opioid receptor compared to Salvinorin A.

Figure 9:
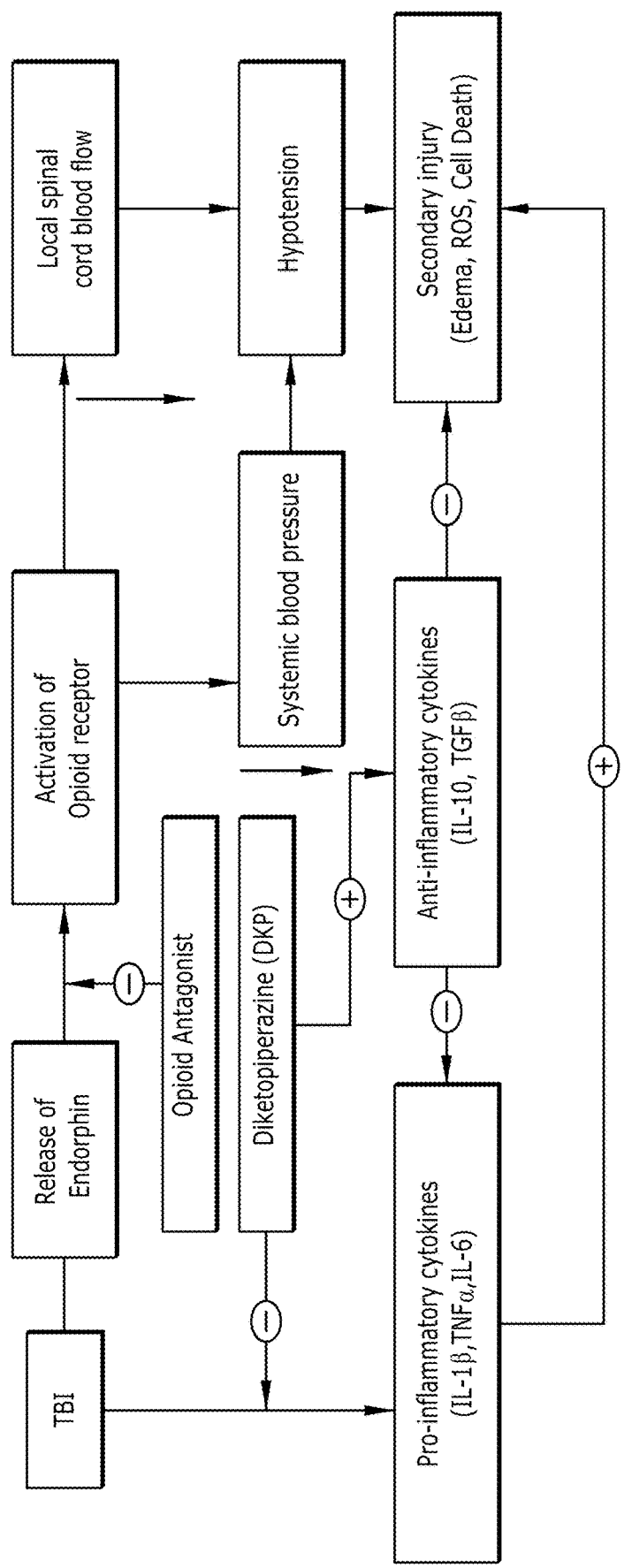
FIG. 9 depicts the neuroprotective mechanism of the gliotoxin analog of the present invention as an opioid antagonist.

Therefore, as described more fully in FIG. 9, the compounds of the present invention are capable of serving as neuroprotectants via opioid receptor antagonism, by blocking activation of opioid receptors and increase of pro-inflammatory cytokines, all of which lead to secondary injury such as edema, ROS, and cell death.

It is another embodiment of the present invention to provide Formula 1b comprising an aqueous solution and one or more pharmaceutically acceptable excipients, additives, carriers or adjuvants. Formula 1b may further comprise one or more excipients, carriers, additives, adjuvants, or binders in a tablet or capsule. Formula 1b may further be administered via an oral, intraperitoneal, intravascular, peripheral circulation, subcutaneous, intraorbital, ophthalmic, intraspinal, intracisternal, topical, infusion, implant, aerosol, inhalation, scarification, intracapsular, intramuscular, intranasal, buccal, transdermal, pulmonary, rectal, or vaginal route.

The compounds of the present invention are capable of treatment in a manner selective to CNS activity and does not manipulate the activity of other CNS receptors, as other CNS drugs have a tendency to do. Therefore, the compounds of the present invention have substantially reduced toxicity profiles (i.e. depression, headache, suicidal thoughts, and the like). The compounds of the present invention are further active as low nanomolar ranges due to its potency.

Those skilled in the art will recognize that the methods and compositions of the present invention may be implemented in many manners and as such are not to be limited by the foregoing exemplary embodiments and examples. In other words, functional elements being performed by single or multiple components, in various combinations of hardware and software or firmware, and individual functions, may be distributed among various software applications at either the client level or server level or both. In this regard, any number of the features of the different embodiments described herein may be combined into single or multiple embodiments, and alternate embodiments having fewer than, or more than, all of the features described herein are possible.

Functionality may also be, in whole or in part, distributed among multiple components, in manners now known or to become known. Thus, myriad combinations are possible in achieving the functions, features, and preferences described herein. Moreover, the scope of the present invention covers conventionally known manners for carrying out the described features as well as those variations and modifications that may be made to the processes, composition, or compounds described herein as would be understood by those skilled in the art now and hereafter.

While various embodiments have been described for purposes of this disclosure, such embodiments should not be deemed to limit the teaching of this disclosure to those embodiments. Various changes and modifications may be made to the elements and operations described above to obtain a result that remains within the scope of the compositions and methods described in this disclosure.

References incorporated by reference herein:
Alan D. Borthwick. 2,5-Diketopiperazines: Synthesis, Reactions, Medicinal Chemistry, and Bioactive Natural Products. Chemical Reviews 2012, 112 (7), 3641-3716.
T. R. Welch, R. M. Williams. Epidithiodioxopiperazines. occurrence, synthesis and biogenesis. Nat. Prod. Rep., 2014, 31(10), 1376-1404.
Scharf, D. H.; Remme, N.; Heinekamp, T.; Hortschansky, P.; Brakhage, A. A.; Hertweck, C. Transannular Disulfide Formation in Gliotoxin Biosynthesis and Its Role in Self-Rresistance of the Human Pathogen *Aspergillus fumigatus*. J. Am. Chem. Soc. 2010, 132, 10136-10141.
Cornacchia C, Cacciatore I, Baldassarre L, Mollica A, Feliciani F, Pinnen F. 2,5-diketopiperazines as neuroprotective agents. Mini-Rev Med Chem. 2012; 12:2-12.
Faden A I, Holaday J W. Opiate antagonists: a role in the treatment of hypovolemic shock. Science. 1979, 205:317-318.

What is claimed is:

1. A compound having a formula:

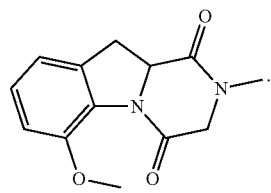 [SMILES: COc1cccc2c1N1C(=O)CN(C)C(=O)C1C2]

2. A method for treating a disorder selected from the group consisting of alcohol dependence, opioid abuse treatment, neurological disorders, neuropathic pain, and fibromyalgia, comprising administering to a patient in need thereof a therapeutically effective amount of a compound of having a formula:

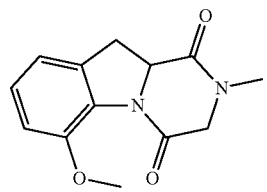 [SMILES: COc1cccc2c1N1C(=O)CN(C)C(=O)C1C2]

or a pharmaceutically acceptable salt thereof or isotopic variants thereof, stereoisomers or tautomers thereof.

3. The method of claim 2, further comprising administering a therapeutically effective amount of said compound sufficient as a non-selective antagonist of opioid receptors.

4. The method of claim 2, wherein administering a therapeutically effective amount of said compound is capable of having at least 50% of the administered amount cross the blood-brain barrier (BBB) of a patient.

5. The method of claim 2, wherein said administered compound is capable of inhibition of CNS receptors selected from the group consisting of mu (μ) opioid receptor, delta (δ) opioid receptor, and kappa (κ) opioid receptor, or combinations thereof.

6. The method of claim 2, wherein said compound is further effective to block or reduce the tolerance of said human to an opioid receptor agonist.

7. The method of claim 6, wherein the opioid receptor agonist is selected from the group consisting of morphine, methadone, codeine, diacetyl morphine, morphine-N-oxide, oxymorphone, oxycodone, hydromorphone, hydrocodone, meperidine, heterocodeine, fentanyl, sufentanil, levo-acetylmethadol, alfentanil, levorphanol, tilidine, diphenoxylate, hydroxymorphone, noroxymorphone, metopon, and propoxyphene, or pharmaceutically acceptable salts thereof.

8. The method of claim 2, wherein said compound is administered via an oral, intraperitoneal, intravascular, peripheral circulation, subcutaneous, intraorbital, ophthalmic, intraspinal, intracisternal, topical, infusion, implant, aerosol, inhalation, scarification, intracapsular, intramuscular, intranasal, buccal, transdermal, pulmonary, rectal, or vaginal route.

9. A method for treating a disorder selected from the group consisting of alcohol dependence, opioid abuse treatment, neurological disorders, neuropathic pain, and fibromyalgia in a patient in need thereof, comprising the step of administering to said patient a pharmaceutical acceptable amount of a compound having the formula:

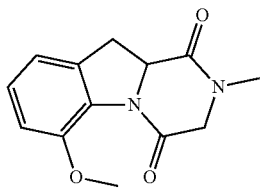 [SMILES: COc1cccc2c1N1C(=O)CN(C)C(=O)C1C2]

or a pharmaceutically acceptable salt thereof or isotopic variants thereof, stereoisomers or tautomers thereof, wherein said pharmaceutically acceptable amount is effective as an antagonist to one or more opioid receptors.

10. The method of claim 9, further comprising administering a therapeutically effective amount of said compound sufficient as a non-selective antagonist of opioid receptors.

11. The method of claim 9, wherein administering a therapeutically effective amount of said compound is capable of having at least 50% of the administered amount cross the blood-brain barrier (BBB) of a patient.

12. The method of claim 9, wherein said administered compound is capable of inhibition of CNS receptors selected from the group consisting of mu (μ) opioid receptor, delta (δ) opioid receptor, and kappa (κ) opioid receptor, or combinations thereof.

13. The method of claim 9, wherein said compound is further effective to block or reduce the tolerance of said human to an opioid receptor agonist.

14. The method of claim 13, wherein the opioid receptor agonist is selected from the group consisting of morphine, methadone, codeine, diacetyl morphine, morphine-N-oxide, oxymorphone, oxycodone, hydromorphone, hydrocodone, meperidine, heterocodeine, fentanyl, sufentanil, levo-acetylmethadol, alfentanil, levorphanol, tilidine, diphenoxylate, hydroxymorphone, noroxymorphone, metopon, and propoxyphene, or pharmaceutically acceptable salts thereof.

15. The method of claim 9, wherein said compound is administered via an oral, intraperitoneal, intravascular, peripheral circulation, subcutaneous, intraorbital, ophthalmic, intraspinal, intracisternal, topical, infusion, implant, aerosol, inhalation, scarification, intracapsular, intramuscular, intranasal, buccal, transdermal, pulmonary, rectal, or vaginal route.

16. A pharmaceutical composition comprising a therapeutically effective amount of the compound of claim 1, or a pharmaceutically acceptable salt, isotopic variants, stereoisomers or tautomers thereof.

17. A pharmaceutical formulation comprising an effective amount of a compound of claim 1 sufficient as a non-selective antagonist of opioid receptors.

18. The compound of claim 1, wherein said compound is capable of having at least 50% of the administered amount cross the blood-brain barrier (BBB) of a patient.

19. The compound of claim 1, wherein said compound is effective to treat alcohol dependence, opioid abuse treatment, neurological disorders, neuropathic pain, and fibromyalgia.

20. The compound of claim 1, wherein said compound is capable of inhibition of CNS receptors selected from the group consisting of mu (μ) opioid receptor, delta (δ) opioid receptor, kappa (κ) opioid receptor, or combinations thereof.

21. The compound of claim 1, wherein said compound is further effective to block or reduce the tolerance of said human to an opioid receptor agonist.

22. The compound of claim 21, wherein the opioid receptor agonist is selected from the group consisting of morphine, methadone, codeine, diacetyl morphine, morphine-N-oxide, oxymorphone, oxycodone, hydromorphone, hydrocodone, meperidine, heterocodeine, fentanyl, sufentanil, levo-acetylmethadol, alfentanil, levorphanol, tilidine, diphenoxylate, hydroxymorphone, noroxymorphone, metopon, and propoxyphene, or pharmaceutically acceptable salts thereof.

* * * * *